US011280006B2

(12) United States Patent
Kim et al.

(10) Patent No.: US 11,280,006 B2
(45) Date of Patent: Mar. 22, 2022

(54) METHOD FOR PREPARING TITANIUM-CONTAINING IMPLANT BY USING ENVIRONMENTALLY-FRIENDLY ETCHING COMPOSITION

(71) Applicant: KYUNGPOOK NATIONAL UNIVERSITY INDUSTRY-ACADEMIC COOPERATION FOUNDATION, Daegu (KR)

(72) Inventors: Kyo Han Kim, Daegu (KR); Tae Yub Kwon, Daegu (KR); Jun Sik Son, Daegu (KR)

(73) Assignee: KYUNGPOOK NATIONAL UNIVERSITY INDUSTRY-ACADEMIC COOPERATION FOUNDATION, Daegu (KR)

(*) Notice: Subject to any disclaimer, the term of this patent is extended or adjusted under 35 U.S.C. 154(b) by 1068 days.

(21) Appl. No.: 15/128,735

(22) PCT Filed: Mar. 18, 2015

(86) PCT No.: PCT/KR2015/002604
§ 371 (c)(1),
(2) Date: Sep. 23, 2016

(87) PCT Pub. No.: WO2015/147473
PCT Pub. Date: Oct. 1, 2015

(65) Prior Publication Data
US 2017/0107627 A1    Apr. 20, 2017

(30) Foreign Application Priority Data

Mar. 25, 2014  (KR) .................. 10-2014-0034865
Oct. 8, 2014   (KR) .................. 10-2014-0136030

(51) Int. Cl.
C23F 1/26    (2006.01)
A61L 31/14   (2006.01)
(Continued)

(52) U.S. Cl.
CPC ............ C23F 1/26 (2013.01); A61L 27/06 (2013.01); A61L 31/022 (2013.01); A61L 31/14 (2013.01); C23F 1/00 (2013.01); A61L 2400/18 (2013.01)

(58) Field of Classification Search
CPC ...... C23F 1/26; C23F 1/00; C23F 1/14; A61L 27/06; A61L 2400/18
(Continued)

(56) References Cited

U.S. PATENT DOCUMENTS 3,280,039 A   10/1966  Smolens et al.
7,883,661 B2  2/2011   Hamman et al.
(Continued)

FOREIGN PATENT DOCUMENTS

EP   2113260     11/2009
WO   2008/033867  3/2008

OTHER PUBLICATIONS

Wikipedia the Free Encyclopedia "Silicon" via https://en.wikipedia.org/wiki/Silicon ; pp. 1-25; 2019.*
(Continued)

*Primary Examiner* — Binh X Tran
(74) *Attorney, Agent, or Firm* — Paratus Law Group, PLLC

(57) ABSTRACT

The present invention provides a method for preparing an implant including preparing a mixed etching composition including hydrogen peroxide and a water-soluble carbonate compound and oxidatively etching an implant made of titanium or a titanium alloy by immersing the same in the
(Continued)

etching composition; a titanium or titanium alloy implant prepared by oxidative etching with a mixed etching composition including hydrogen peroxide and a water-soluble carbonate compound; and a composition for treating surface of an implant containing hydrogen peroxide and a water-soluble carbonate compound. Further, the present invention relates to a titanium or titanium alloy implant which is prepared by oxidative etching with a mixed etching composition including hydrogen peroxide and a basic solution and on which surface bumps having continuous or discontinuous line-shaped open channel structures in nanoscale are irregularly formed, and a preparation method thereof. The surface of the titanium alloys treated with the mixed etching composition including hydrogen peroxide and a carbonate compound or the etching composition containing hydrogen peroxide and a basic solution of the present invention includes micrometer-sized bumps and channel-shaped nanometer-sized bumps, and thus has an increased surface area, and can not only improve wettability, but also effectively promote cell proliferation and osteocyte differentiation. In addition, the composition includes no chemical compounds such as a strong acid, etc. and is thus environmentally friendly, and such compounds can be prevented from remaining on the surface, which can improve biocompatibility, and therefore, the composition can be useful for implant surface treatment.

9 Claims, 11 Drawing Sheets

(51) Int. Cl.
A61L 31/02 (2006.01)
A61L 27/06 (2006.01)
C23F 1/00 (2006.01)

(58) Field of Classification Search
USPC .................................... 216/100, 102
See application file for complete search history.

(56) References Cited

U.S. PATENT DOCUMENTS

2009/0204213 A1* 8/2009 Liao ............... A61F 2/30767
623/11.11
2011/0233169 A1* 9/2011 Mayfield ............ A61C 8/0012
216/37
2012/0129129 A1 5/2012 Fehr et al.

OTHER PUBLICATIONS

Ok H. Ryu et al. "Gingival Epithelial Cell Expression of Macrophage Inflammatory Protein-1α Induced by Interleukin-1β Lipopolysaccharide", J Periodontol Aug. 2007 via https://onlinelibrary.wiley.com/doi/epdf/10.1902/jop.2007.070066 ; pp. 1627-1634; 2007.*
Wikipedia the Free Encyclopedia, "Bone" via https://en.wikipedia.org/wiki/Bone ; pp. 1-18; 2019.*
Ti 6Al—4V ELI via https://www.fwmetals.com/services/resource-library/ti-6al-4v-eli/; pp. 1-4; No. date available.*
Extended European Search Report in corresponding European Application Serial No. 15768577.7, dated Sep. 11, 2017.
Zhang, et al., "Effect of heat treatment on H2O2/HCl etched pure titanium dental implant: An in vitro study," Med. Sci. Monit, vol. 18, issue 7, 201, pp. 265-272.
Amigo, et al., "Microstructural evolution of Ti—6Al—4V during the sintering of microspheres of Ti for orthopedic implants," Journal of Materials Processing Technology, vol. 141, 2003, pp. 117-122.
Kim, et al., "Effect of heat treatment on apatite-forming ability of Ti metal induced by alkali treatment," Journal of Materials Science: Materials in Medicine, vol. 8, 1997, pp. 341-347.
Popa, et al., "Titanium—hydroxyapatite porous structures for endosseous applications,"Journal of Materials Science: Materials in Medicine, vol. 16, 2005, pp. 1165-1171.
Lee, et al., "Surface Characteristics and Bioactivity of Anodically Oxidized Titanium Surfaces," Acad. Prosthodont., vol. 45, issue 1, 2007, pp. 85-97, (English abstract attached).
Rautray, et al., "Surface Modification of Titanium and Titanium Alloys by Ion Implantation," Journal of Biomed. Mater. Res B Appl. Biomater., vol. 93, issue 2, 2010, pp. 581-591.
Vetrone, et al., "Nanoscale Oxidative Patterning of Metallic Surfaces to Modulate Cell Activity and Fate," Nano Letters, vol. 9, issue 2, 2009, pp. 659-665.
PCT/KR2015/002604 International Search Report dated Jul. 1, 2015 (English translation attached).

* cited by examiner

[FIG. 1]
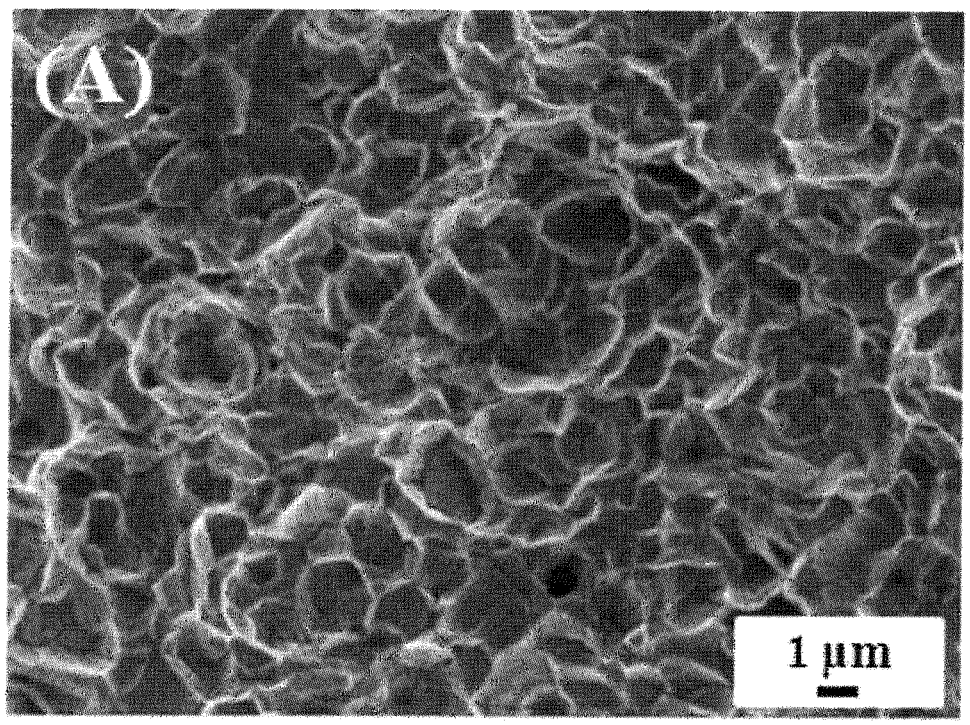
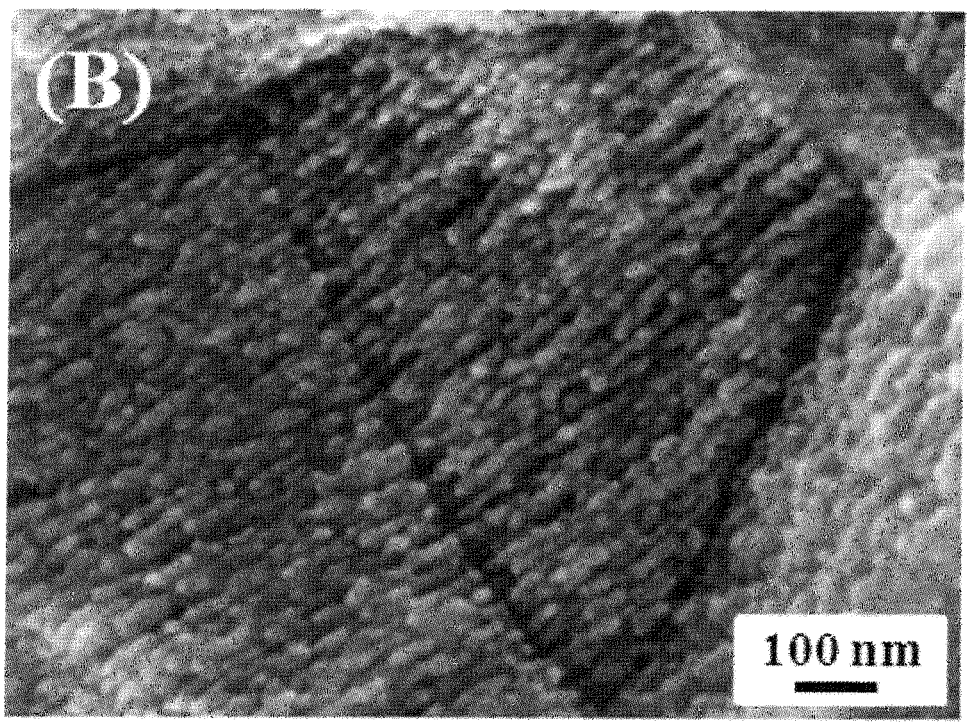

[FIG. 2]
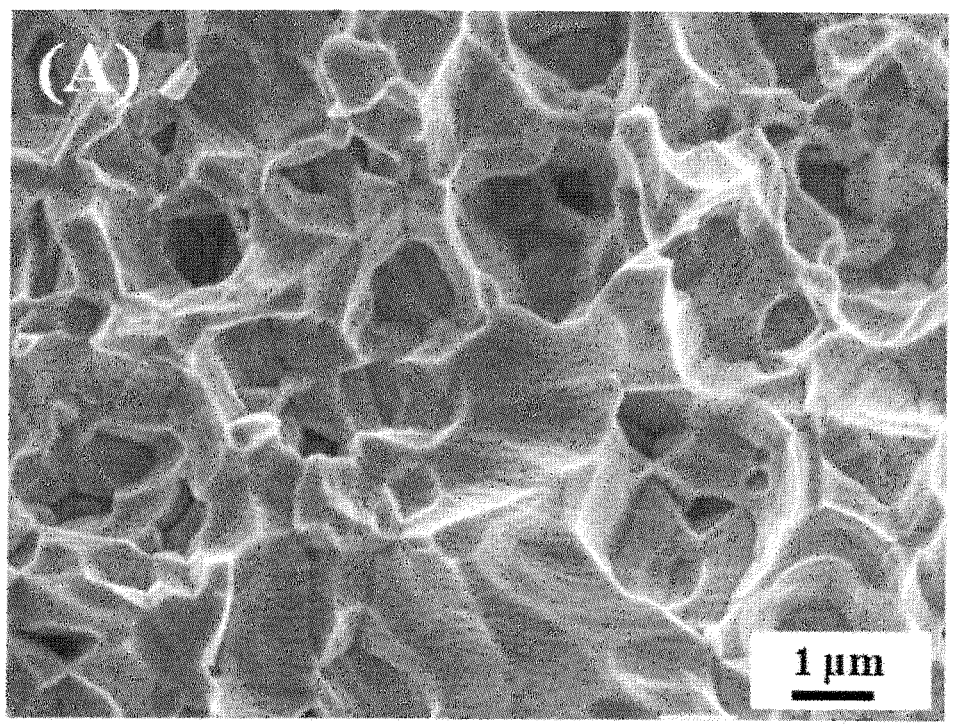
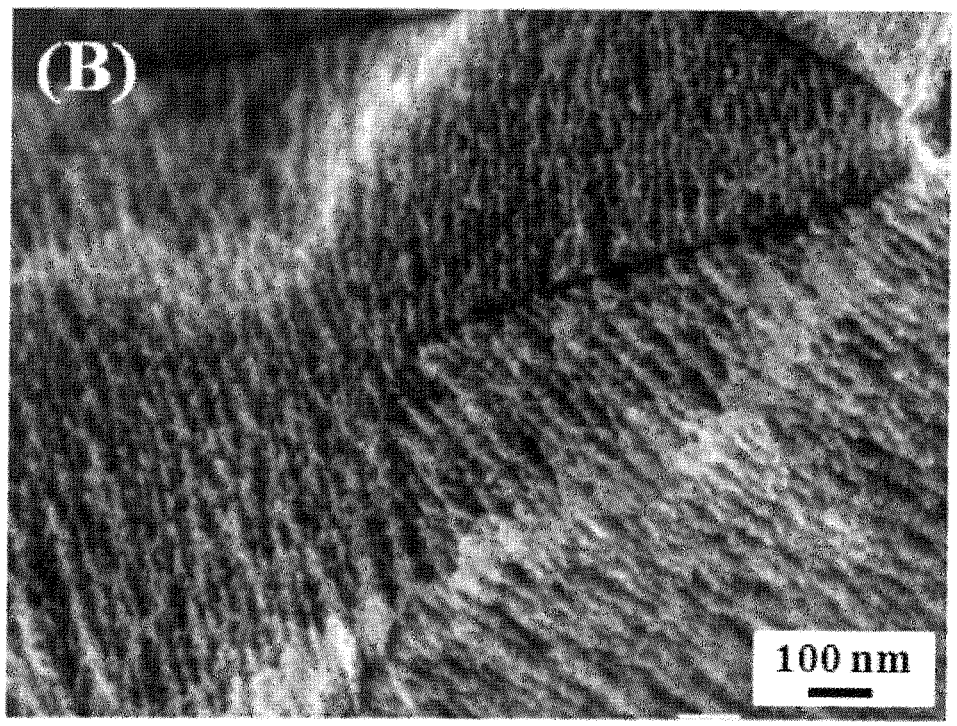

[FIG. 3]
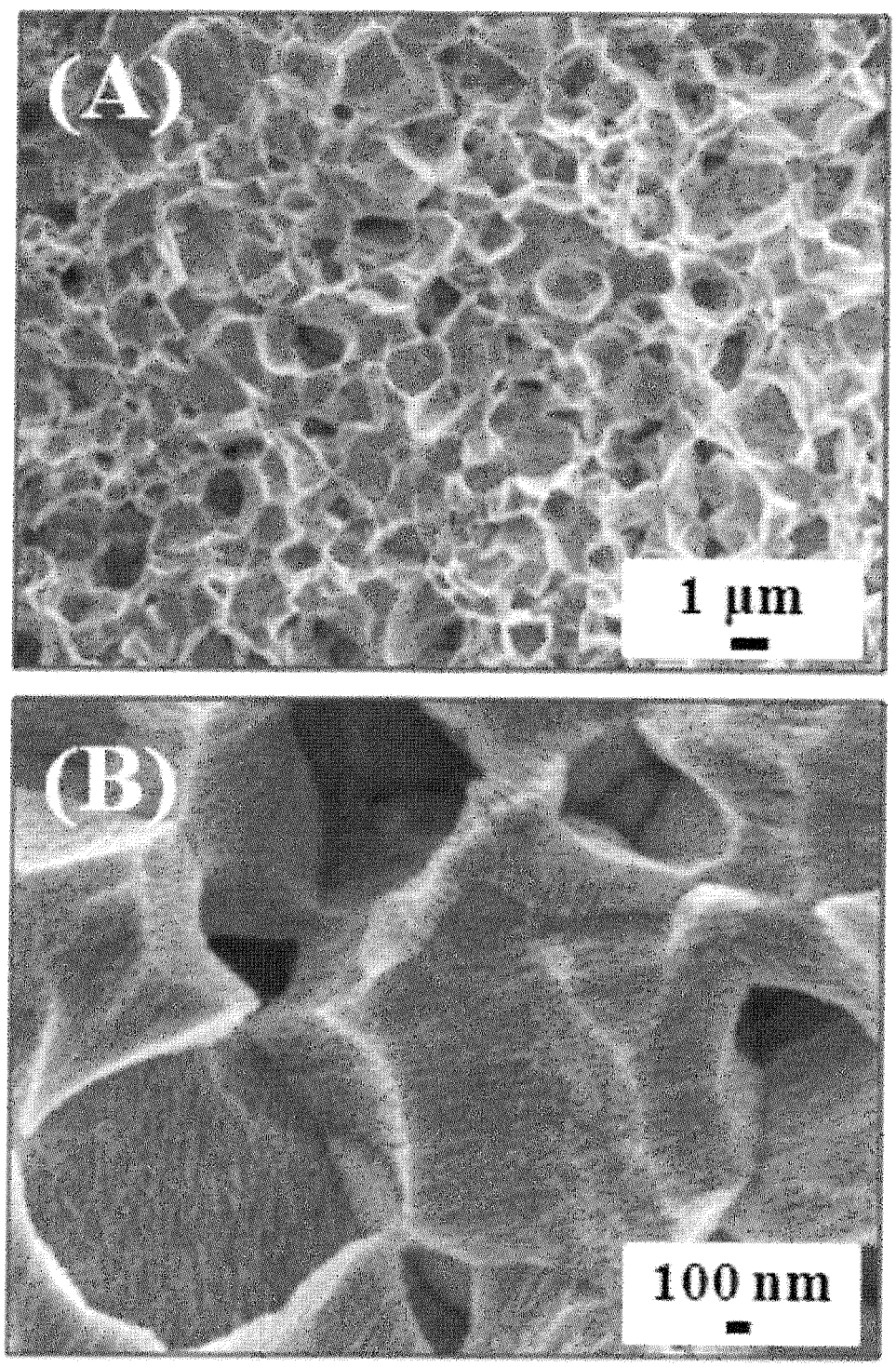

[FIG. 4]
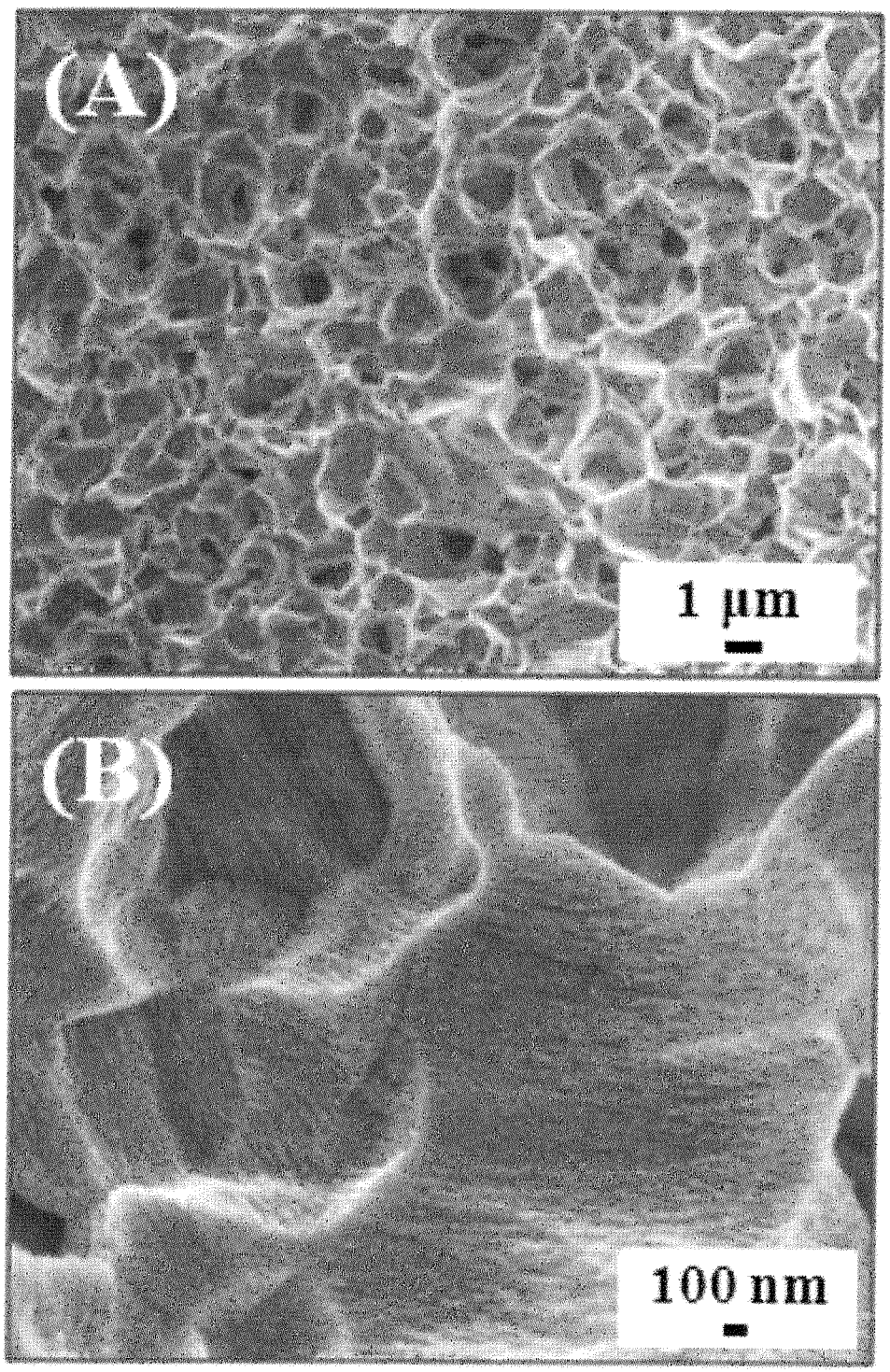

[FIG. 5]
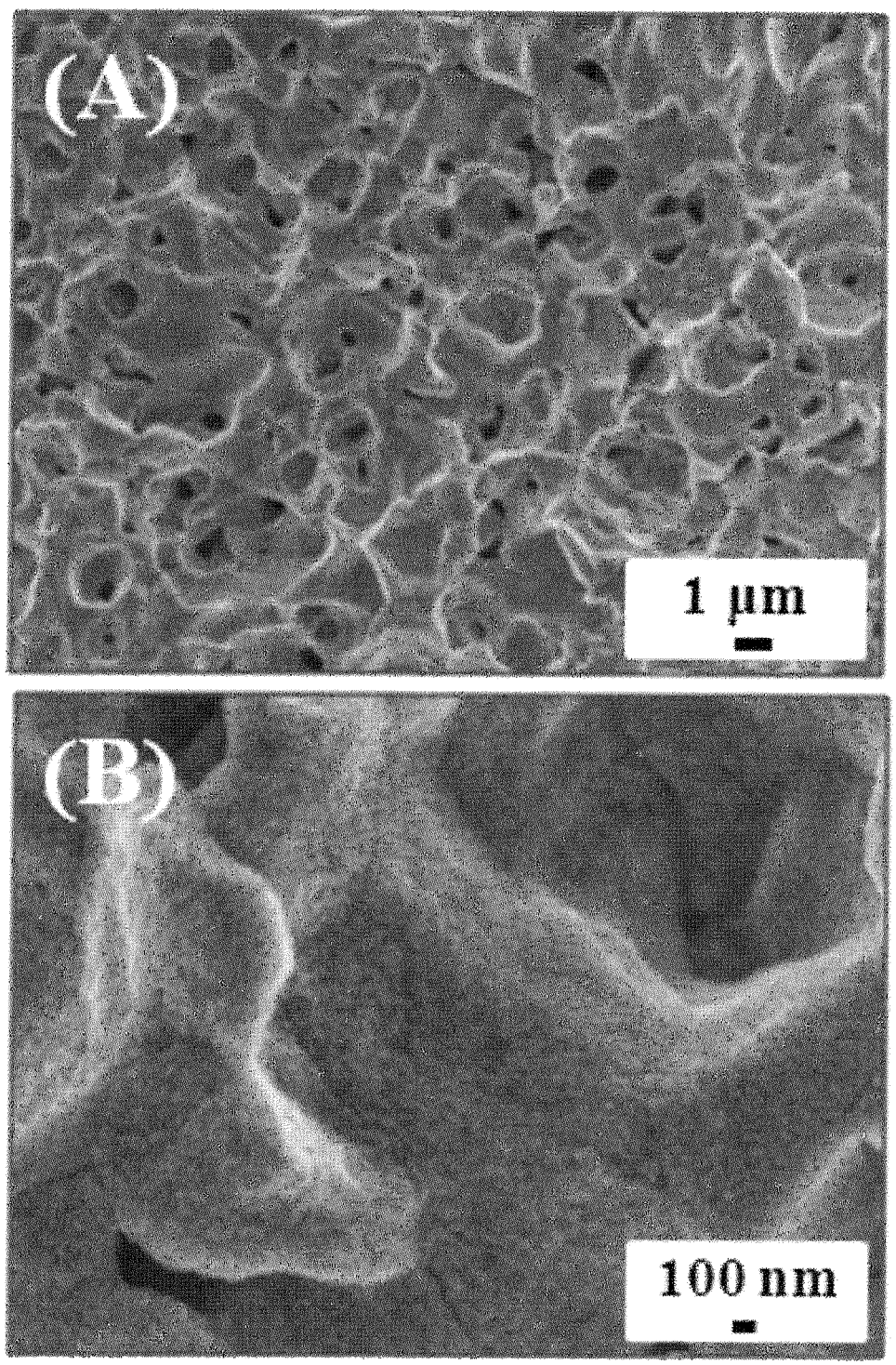

[FIG. 6]
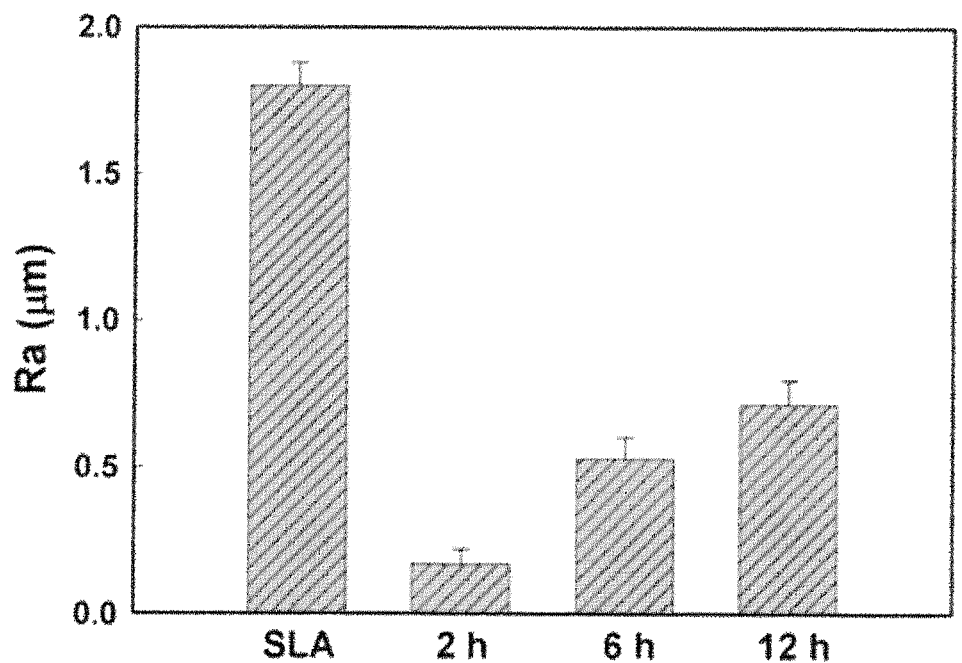

[FIG. 7]
(A)
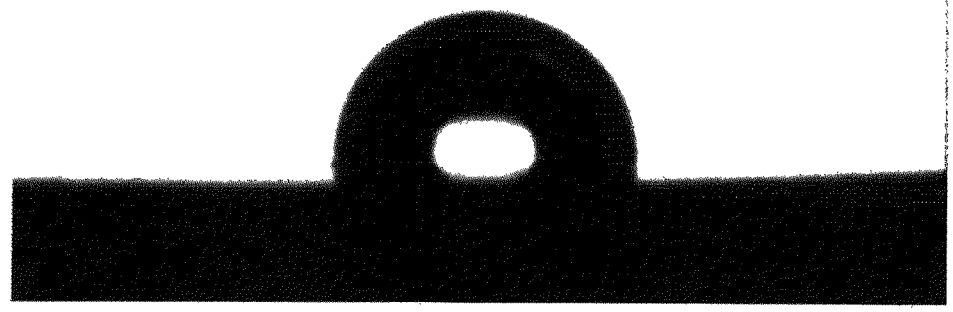
(B)
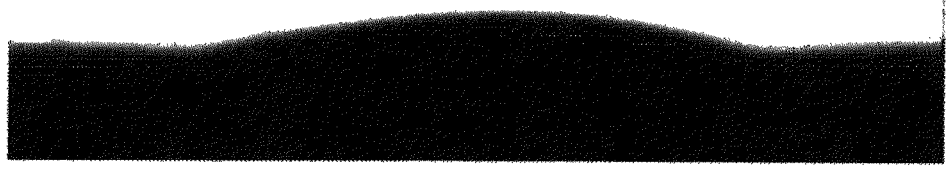

[FIG. 8]
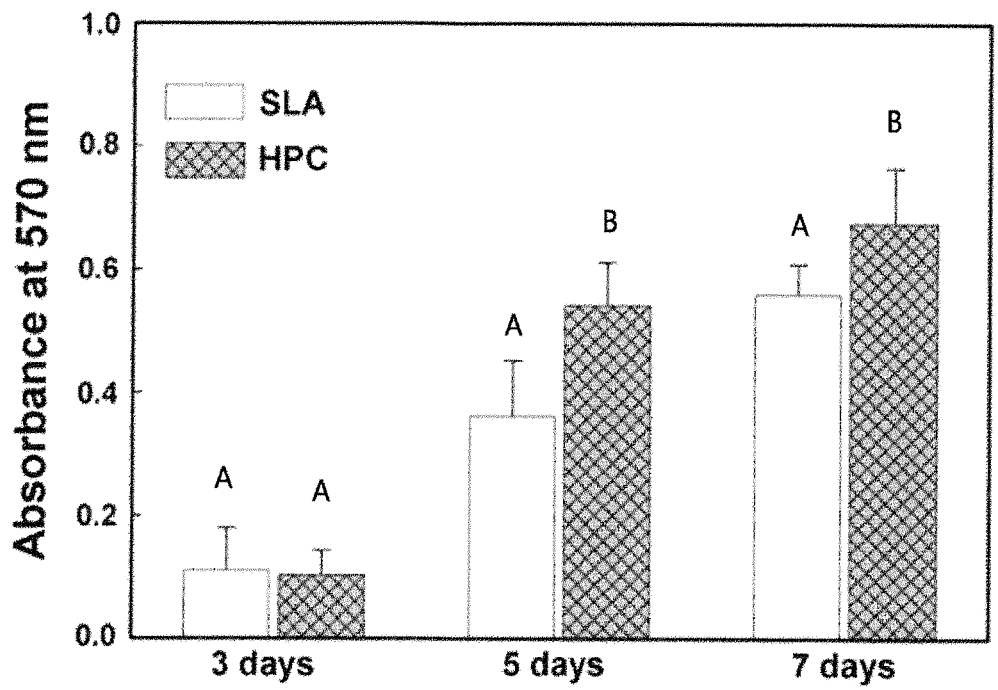
[FIG. 9]
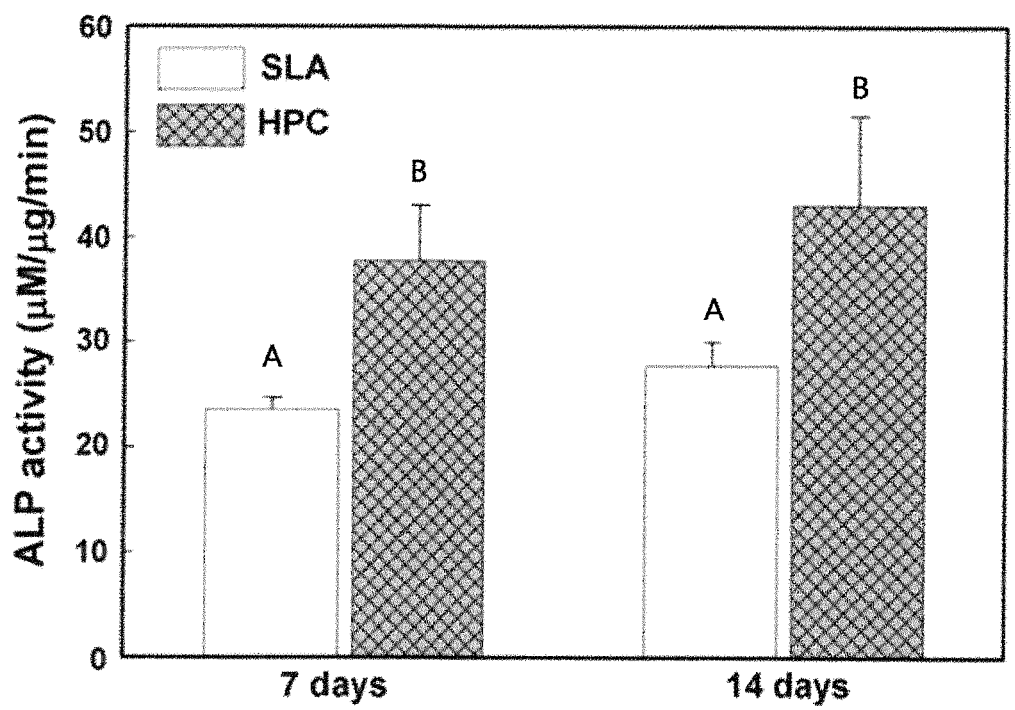

[FIG. 10]
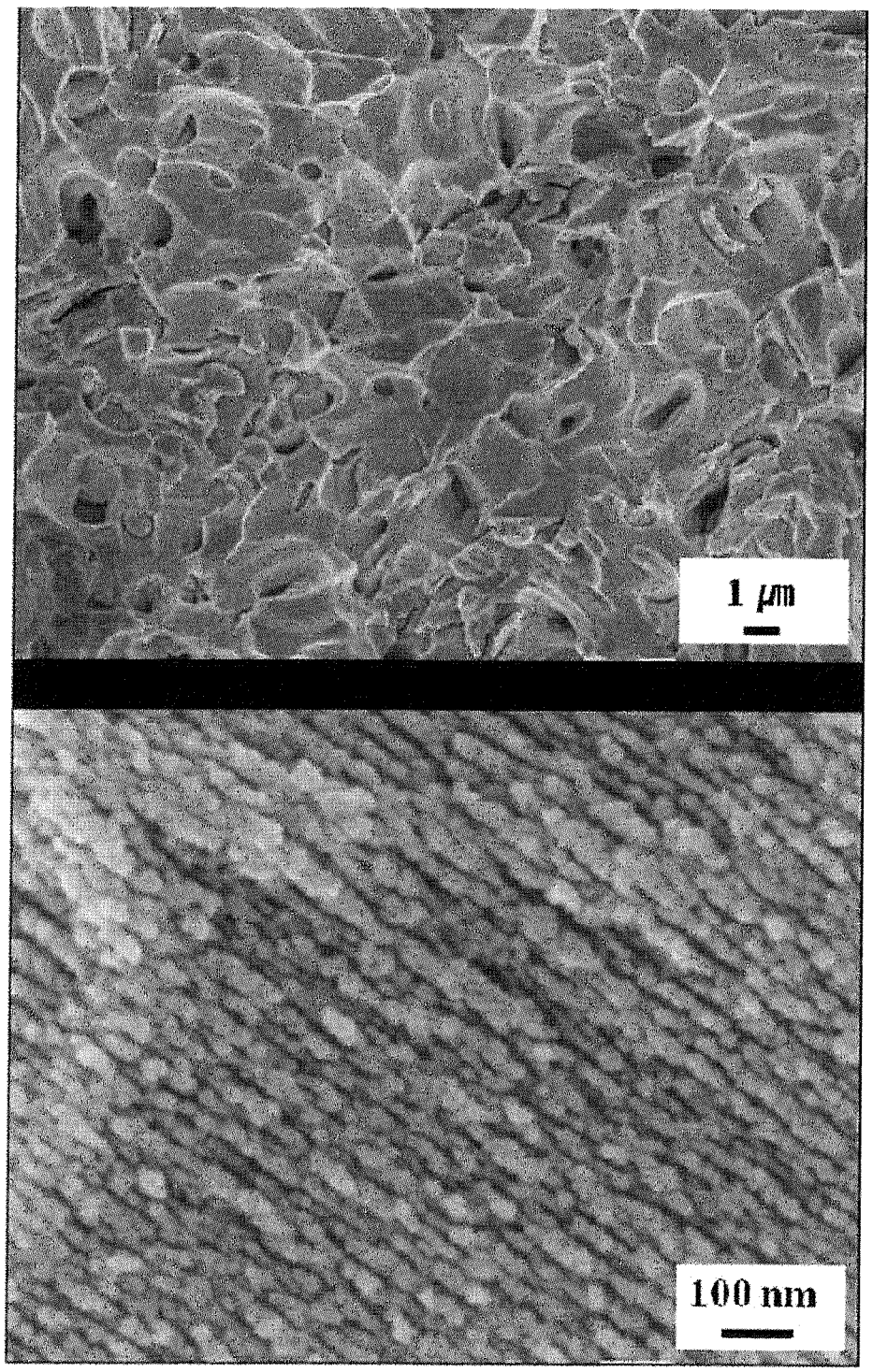

[FIG. 11]
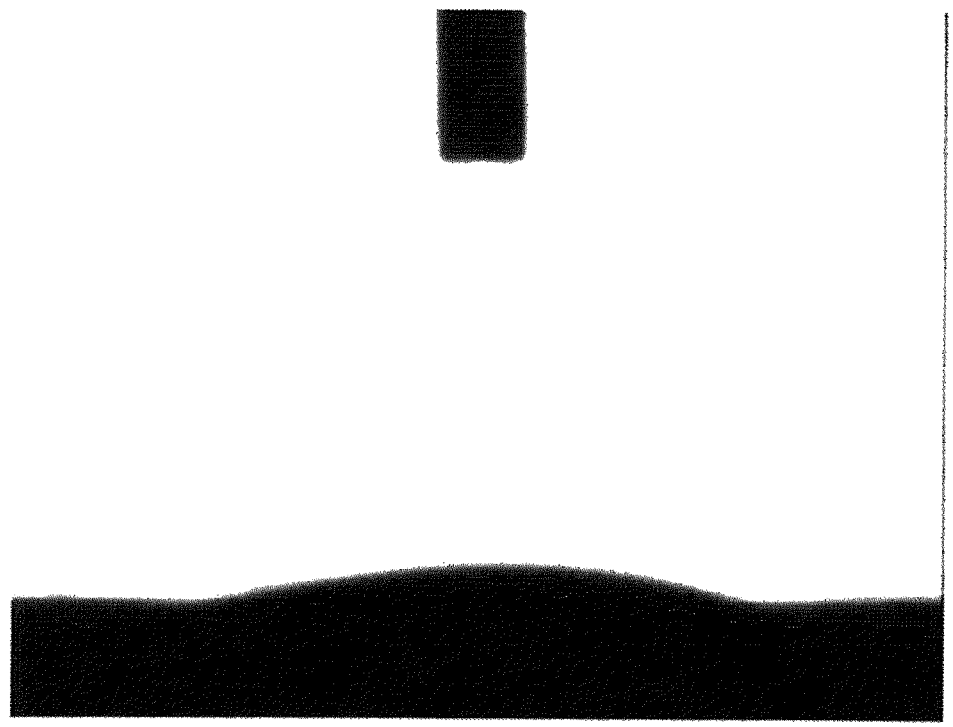

[FIG. 12]
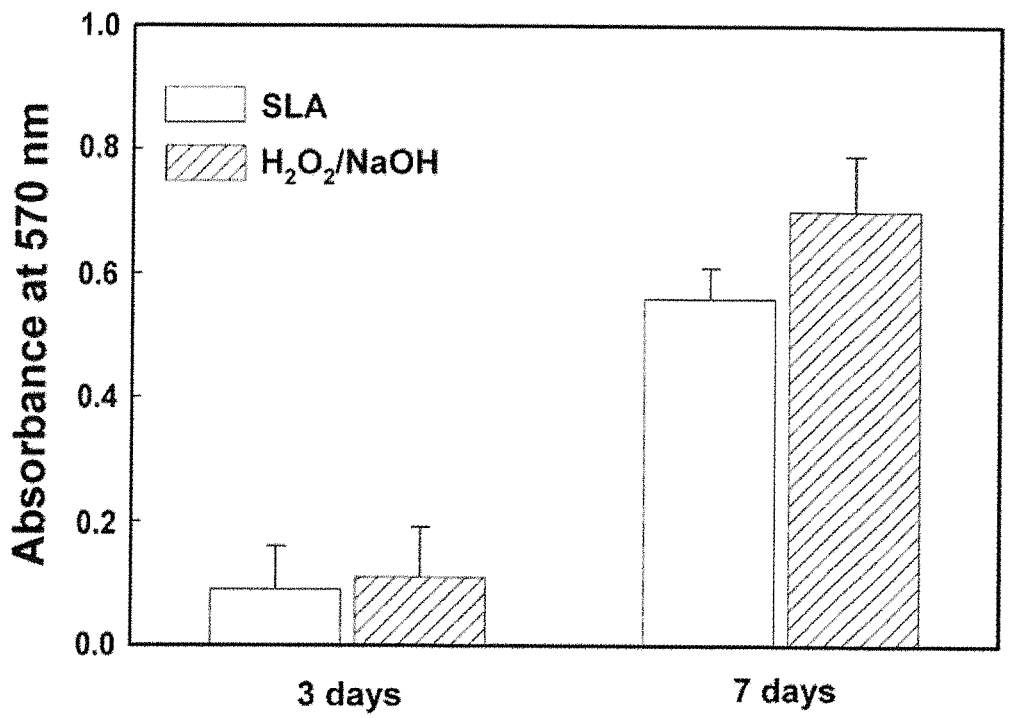
[FIG. 13]
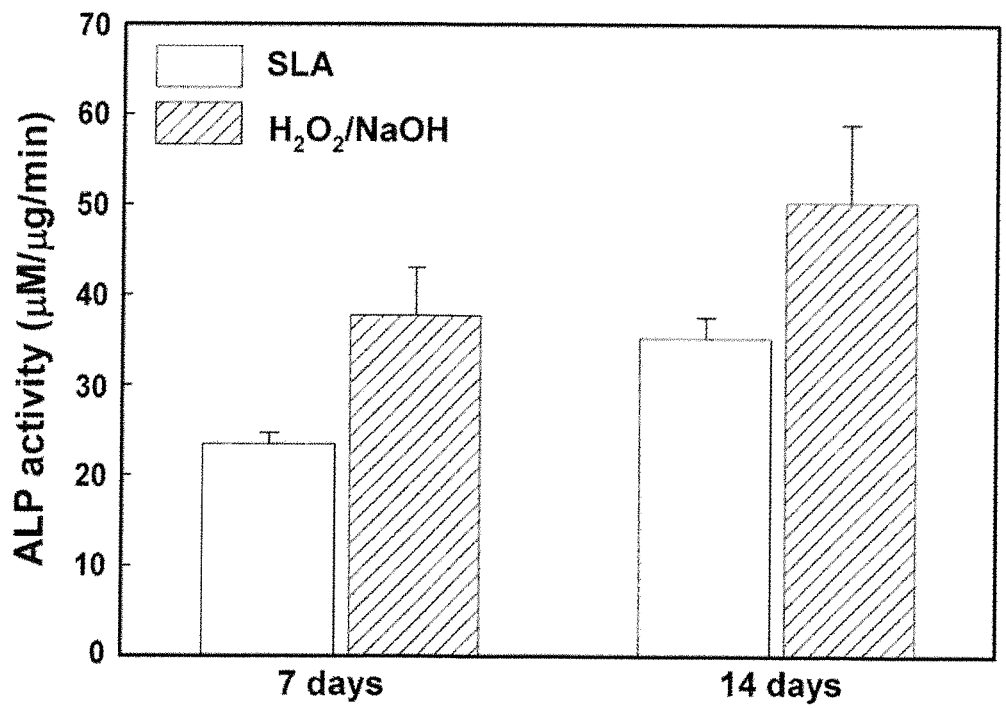

METHOD FOR PREPARING TITANIUM-CONTAINING IMPLANT BY USING ENVIRONMENTALLY-FRIENDLY ETCHING COMPOSITION

RELATED APPLICATIONS

This application is the National Stage of International Patent Application No. PCT/KR2015/002604, filed Mar. 18, 2015, which is hereby incorporated by reference in its entirety, and which claims priority to Korean Patent Application No. 10-2014-0034865, filed Mar. 25, 2014 and Korean Patent Application No. 10-2014-0136030, filed Oct. 8, 2014.

TECHNICAL FIELD

The present invention relates to a titanium or titanium alloy implant prepared by oxidative etching with a mixed etching composition including hydrogen peroxide and a water-soluble carbonate compound; a preparation method thereof; and a composition for treating a surface of an implant containing hydrogen peroxide and a water-soluble carbonate compound.

Further, the present invention relates to a titanium or titanium alloy implant which is prepared by oxidative etching with a mixed etching composition including hydrogen peroxide and a basic solution and on which surface bumps having continuous or discontinuous line-shaped open channel nanoscale structures are irregularly formed; and a preparation method thereof.

BACKGROUND ART

Metals or alloys for bio-implantation have excellent strength, fatigue resistance, and formability compared to other materials such as ceramics and polymers, and thus are the most widely used biomaterials in dentistry, orthopedics, and plastic surgery to date for the purpose of regenerating and treating bone defects and damages. Metals or alloys include iron, chromium, nickel, stainless steel, cobalt-based alloys, titanium, titanium alloys, zirconium, niobium, tantalum, gold, silver, etc. Among these metals or alloys, titanium and titanium alloys, etc. are highly resistant to corrosion and stable in human tissues, and thus are the most widely used implant materials in dentistry, orthopedics, and plastic surgery.

Attempts have been made for the last several years to improve osseointegration by increasing the surface area of the metals or alloys, changing the surface topography, or by physical, chemical, or biological surface treatments, in order to improve biocompatibility in tissues when inserted into the body. The osseointegration refers to the direct structural and functional connection between the intrinsic bone tissue of a patient and an inserted implant, and a strong integration of the implant surfaces with the bone tissue is an essential factor which improves the durability of the implant in the body, thereby enabling a long-term clinical function.

Since the 1990s, extensive efforts have been steadily made to facilitate various surface modifications as a method for improving the integration with bone tissues, while minimizing the bone resorption around the metal or alloy implant and improving the affinity and binding force with surrounding soft tissues. Specifically, the representative surface treatment methods widely used for titanium and titanium alloys include metal bead sintering (V. Amigo et al., J. Mater. Process. Technol., 2003, 141(1): 117-122), blasting and acid treatment (J. E. Feighan et al., J. Bone Joint Surg. Am., 1995, 77(9): 1380-1395), alkali immersion and heat treatment (H. M. Kim et al., J. Mater. Sci. Mater. Med., 1997, 8(6): 341-347), hydroxyapatite coating (C. Popa et al., J. Mater. Sci. Mater. Med., 2005, 16(12): 1165-1171), anodic oxidation (S. H. Lee et al., J. Kor. Acad. Prosthodont., 2007, 45(1): 85-97), ion implantation (T. R. Rautray et al., J. Biomed. Mater. Res. B Appl. Biomater., 2010, 93(2): 581-591), etc., and recently, the most widely used method is SLA (sandblasted, large-grit, acid etched) method.

The SLA is a method for improving surface area by a large-grit sandblasting technique using ceramic particles in which a micro-roughness is formed on the titanium alloy surface, followed by acid etching which further forms a small micro-roughness. The characteristic of the SLA surface treatment is that various sizes of micrometer-sized pores form sponge-like network structures, and thus, it has advantages in that new bone has an excellent initial fixing force, the bone can be easily integrated, and the degree of osseointegration is high even after healing. However, it can be problematic in that the ceramic particles treated by the large-grit sandblasting (alumina or hydroxyapatite (HA)) remain on the surface and can thus serve as impurities, and chemical substances after treatment with a strong acid remain on the surface, or fractures may appear at the interface of metal particles, etc. Further, since the method includes the treatment with a strong acid, it is harmful to humans and may cause environmental pollution. In addition, it may be problematic as it requires several washing processes in order to remove the chemical substances remaining on the titanium surface after surface treatment, and thus it may be the cause of energy waste, increasing the production cost of the implant.

Meanwhile, the quality of a dental implant is determined by chemical, physical mechanical, and geographical properties of the surface thereof. In general, it is well known that the surface topography influences cell growth, osteoblastic differentiation, and bone tissue formation, the surface roughness influences cell migration and proliferation, and the surface chemistry has an impact on protein adsorption and cell activity. A macro-roughness formed on the titanium surface (roughness with a size of several tens of micrometers to several millimeters) is directly related to the geometry of an implant having a thread, and when such macro-roughness is appropriately formed on the implant surface, the initial binding force and extended physical stability thereof can increase. In addition, the mechanical interlocking between the implant surface and its surrounding tissues can be improved. A micro-roughness formed on the titanium surface (micro-roughness with a size of hundreds of nanometers to tens of micrometers) can maximize the interlocking between the implant surface and mineralized bones. Further, a nano-roughness (roughness with a size of several nanometers to several tens of nanometers) and nanoscale topography have a major impact on protein absorption of the implant surface, osteoblast adhesion, and osseointegration speed. Furthermore, the nano-roughness and nanoscale topography increase surface energy, thereby improving wettability of the implant surface, and facilitate the cellular adhesion and the binding between a protein substrate with fibrin, thereby controlling osteoblastic differentiation.

However, the conventional physical and chemical surface treatment methods for the titanium alloy implants described above cannot give rise to the nanometer-sized roughness. Recently, the research for forming nanometer-sized patterns on the titanium alloy surface by oxidative etching using a composition, in which an acid and hydrogen peroxide are mixed, are currently in progress, but there is a high risk due to the use of a strong acid and a possibility of exposure to toxic substances, and most of all, there is a limitation in preparing satisfiable nanometer-sized patterns (F. Vetrone et al., Nano Lett., 2009, 9(2): 659-665).

DISCLOSURE

Technical Problem

The present inventors have made extensive efforts to find a method for providing a micro/nano texture on an implant surface by a surface treatment using a composition which does not include a strong acid and can thus be handled without risk and which is environmentally friendly, and as a result, it was confirmed that desired micro/nano bump structures can be formed by immersing an implant for a fixed time in a mixed etching composition including hydrogen peroxide and a carbonate compound, and that cell proliferation and bone differentiation can improve on the surface treated as above, thereby completing the present invention.

Further, the present inventors have discovered that even when an implant made of titanium or a titanium alloy was subject to oxidative etching by immersing the same in an etching composition containing hydrogen peroxide and a basic solution, an implant can be prepared on which microscale bumps and/or bumps having continuous or discontinuous line-shaped open channel nanoscale structures are irregularly formed. The present invention is based on these findings.

Technical Solution

A first aspect of the present invention provides a method for preparing an implant comprising: preparing a mixed etching composition comprising hydrogen peroxide and a water-soluble carbonate compound; and oxidatively etching an implant made of titanium or a titanium alloy by immersing the same in the etching composition.

A second aspect of the present invention provides a titanium or titanium alloy implant which is prepared by oxidative etching with the mixed etching composition comprising hydrogen peroxide and a water-soluble carbonate compound.

A third aspect of the present invention provides a composition for treating a surface of an implant comprising hydrogen peroxide and a water-soluble carbonate compound.

A fourth aspect of the present invention provides a method for preparing an implant on which surface bumps having continuous or discontinuous line-shaped open channel nanoscale structures are irregularly formed, wherein the method comprises preparing an etching composition comprising hydrogen peroxide and a basic solution; and oxidatively etching an implant made of titanium or titanium alloys by immersing the same in the etching composition.

A fifth aspect of the present invention provides a titanium or titanium alloy implant which is prepared by oxidative etching with a mixed etching composition comprising hydrogen peroxide and a basic solution and on which surface bumps having continuous or discontinuous line-shaped open channel nanoscale structures are irregularly formed.

Advantageous Effect

The surface of a titanium alloy treated with the mixed etching composition including hydrogen peroxide and a carbonate compound or the etching composition containing hydrogen peroxide and a basic solution of the present invention includes micrometer-sized bumps and channel-shaped nanometer-sized bumps, and thus has an increased surface area, and can not only improve wettability, but also effectively promote cell proliferation and osteocyte differentiation. In addition, the composition includes no chemical compounds such as a strong acid, etc., and is thus environmentally friendly, and such compounds can be prevented from remaining on the surface, which can improve biocompatibility, and therefore, the composition can be useful for implant surface treatment.

BRIEF DESCRIPTION OF FIGURES

FIG. 1 shows SEM results of the surface of the titanium alloys treated with a mixed etching composition including peroxide ($H_2O_2$) and sodium bicarbonate ($NaHCO_3$) according to Example 1 of the present invention. (A) shows micrometer-sized sponge-like network structures of the surface, and (B) shows channel-shaped nanometer-sized bumps formed on the micrometer-sized bumps above.

FIG. 2 shows SEM results of the surface of the titanium alloys treated with a mixed etching composition including hydrogen peroxide and ammonium bicarbonate ($NH_4HCO_3$) according to Example 2 of the present invention. (A) shows micrometer-sized sponge-like network structures of the surface, and (B) shows channel-shaped nanometer-sized bumps formed on the micrometer-sized bumps above.

FIG. 3 shows SEM results of the surface of the titanium alloys treated with a mixed etching composition including hydrogen peroxide and magnesium bicarbonate ($Mg(HCO_3)_2$) according to Example 3 of the present invention. (A) shows micrometer-sized sponge-like network structures of the surface, and (B) shows channel-shaped nanometer-sized bumps formed on the micrometer-sized bumps above.

FIG. 4 shows SEM results of the surface of the titanium alloys treated with a mixed etching composition including hydrogen peroxide and calcium carbonate ($CaCO_3$) according to Example 4 of the present invention. (A) shows micrometer-sized sponge-like network structures of the surface, and (B) shows channel-shaped nanometer-sized bumps formed on the micrometer-sized bumps above.

FIG. 5 shows SEM results of the surface of the titanium alloys treated with a mixed etching composition including hydrogen peroxide and sodium carbonate ($Na_2CO_3$) according to Example 5 of the present invention. (A) shows micrometer-sized sponge-like network structures of the surface, and (B) shows channel-shaped nanometer-sized bumps formed on the micrometer-sized bumps above.

FIG. 6 is a graph showing roughness measured from the surface of the titanium alloys each treated for different time (2 hrs, 6 hrs, and 12 hrs) according to Examples 3 to 5 of the present invention and the surface of the titanium alloys treated according to Comparative Example 1.

FIG. 7 is a graph showing water contact angle of the surface-treated titanium alloys according to Example 1 of the present invention and Comparative Example 1.

FIG. 8 is a graph showing the proliferation rate of cells cultured on the surface-treated titanium alloy discs according to Example 1 of the present invention and Comparative Example 1.

FIG. 9 is a graph showing ALP activity of cells cultured on the surface-treated titanium alloy discs according to Example 1 of the present invention and Comparative Example 1.

FIG. 10 shows images of the surface of the implant treated with an etching composition containing hydrogen peroxide and NaOH according to Example 10 of the present invention.

FIG. 11 is a graph showing water contact angel of the titanium alloys treated with an etching composition containing hydrogen peroxide and NaOH according to Example 10 of the present invention.

FIG. 12 is a graph showing the proliferation rate of cells cultured on the surface-treated titanium alloy discs according to Example 10 of the present invention and Comparative Example FIG. 13 is a graph showing ALP activity of cells cultured on the surface-treated titanium alloy discs according to Example 10 and Comparative Example 1

BEST MODE FOR CARRYING OUT INVENTION

A method for preparing an implant according to the first aspect of the present invention comprises preparing a mixed etching composition comprising hydrogen peroxide and a water-soluble carbonate compound; and oxidatively etching an implant made of titanium or a titanium alloy by immersing the same in the etching composition.

Preferably, the hydrogen peroxide is not limited to a form and/or a composition as long as it is dissolved in a solvent including water and supplied in the form of an aqueous solution with a constant concentration. For example, the hydrogen peroxide may be an aqueous solution of hydrogen peroxide, in which hydrogen peroxide is diluted in water, solid hydrogen peroxide freezed at low temperature, urea hydrogen peroxide ($CO(NH_2)_2 \cdot H_2O_2$), which is an effervescent compound in which hydrogen peroxide is bonded to an organic/inorganic compound, and sodium percarbonate ($2Na_2CO_3 \cdot 3H_2O_2$), or a mixture thereof, but is not limited thereto.

Preferably, the water-soluble carbonate compound may be a bicarbonate compound, a carbonate compound, and a mixture thereof. Compounds capable of providing a bicarbonate ($HCO_3^-$) or a carbonate ($CO_3^{2-}$) anion in an aqueous phase regardless of the type of cation may be used as the carbonate compound without limitation. The non-limiting examples of the bicarbonate compound includes ammonium bicarbonate (($NH_4$)$HCO_3$), sodium bicarbonate ($NaHCO_3$), potassium bicarbonate ($KHCO_3$), magnesium bicarbonate ($Mg(HCO_3)_2$), and calcium bicarbonate ($Ca(HCO_3)_2$). In addition, the non-limiting examples of the carbonate compound includes carbonic acid ($H_2CO_3$), calcium carbonate ($CaCO_3$), lithium carbonate ($Li_2CO_3$), sodium carbonate ($Na_2CO_3$), potassium carbonate ($K_2CO_3$), rubidium carbonate ($Rb_2CO_3$), cesium carbonate ($Cs_2CO_3$), barium carbonate ($BaCO_3$), beryllium carbonate ($BeCO_3$), manganese carbonate ($MnCO_3$), iron carbonate ($FeCO_3$), cobalt carbonate ($CoCO_3$), nickel carbonate ($NiCO_3$), copper carbonate ($CuCO_3$), silver carbonate ($Ag_2CO_3$), zinc carbonate ($ZnCO_3$), cadmium carbonate ($CdCO_3$), aluminum carbonate ($Al_2(CO_3)_3$), thallium carbonate ($Tl_2CO_3$), lead carbonate ($PbCO_3$), lanthanum carbonate ($La_2(CO_3)_3$), and ammonium carbonate (($NH_4$)$_2CO_3$).

The hydrogen peroxide may be included in an amount of 1 wt % to 98 wt % relative to the total weight of the composition. Preferably, the hydrogen peroxide may be included in an amount of 5 wt % to 50 wt %, and more preferably, in an amount of 10 wt % to 50 wt %, but is not limited thereto.

The carbonate compound may be included in an amount of 0.01 wt % to 90 wt % relative to the total weight of the composition. Preferably, the carbonate compound may be included in an amount of 0.1 wt % to 30 wt %, and more preferably, in an amount of 0.5 wt % to 20 wt %, but is not limited thereto.

The pH of the mixed etching composition is dependent on the amount of the carbonate compound comprised. That is, the pH of the mixed etching composition can be regulated by regulating the amount of the carbonate compound comprised. Herein, the mixed etching composition may be regulated to have a pH range of 2 to 8. Preferably, the mixed etching composition may be regulated to have a pH range of 4 to 8, and more preferably, the mixed etching composition may be regulated to have a pH range of 6 to 8, but is not limited thereto.

When the mixed etching composition is left at room temperature, the pH can increase up to a certain level depending on time. Therefore, the composition having a pH range of 7 to 8 can be used when the mixed etching composition is prepared by mixing hydrogen peroxide and the carbonate compound with a solvent containing water, followed by allowing it to stand at room temperature for a certain amount of time.

In the present invention, an "implant" refers to a graft or an insert, and replaces a lost biological tissue, supports a damaged biological tissue, or includes a man-made device manufactured to act as a tissue. The surface of the implant makes contact with the body, and thus can be made of biomedical materials such as titanium, silicon, or hydroxyapatite. If necessary, for example, the implant may be internally equipped with an electronic device as in a pacemaker or cochlear implant, or it may be bioactive as a subcutaneous drug delivery device having the form of an implantable pill or drug-eluting stent. The implant can be accompanied by side effects such as infection, inflammation, and pain as it is intended to be inserted into the body. In addition, it may be recognized as a foreign substance and can thus cause rejection, or may lead to coagulation or an allergic reaction. Therefore, it is very important that a material which can minimize the side effects is selected.

The implant of the present invention may be made of pure titanium metal or alloys mainly containing titanium metal. Preferably, the titanium alloys may further include at least one metal selected from the group consisting of aluminum (Al), tantalum (Ta), niobium (Nb), vanadium (Va), zirconium (Zr), tin (Sn), molybdenum (Mo), silicon (Si), gold (Au), palladium (Pd), copper (Cu), platinum (Pt), and silver (Ag), but are not limited thereto. More preferably, the titanium alloys may be alloys mainly containing titanium and at least one other metal. For example, they may be alloys including aluminum and vanadium; alloys including aluminum and niobium; alloys including niobium and zirconium; alloys including aluminum, molybdenum, and vanadium; alloys including aluminum, vanadium, and tin; alloys including niobium, tantalum, and zirconium; alloys including niobium, tantalum, and tin; alloys including niobium, tantalum, and molybdenum; alloys including aluminum, zirconium, molybdenum, and silicon; alloys including aluminum, tin, zirconium, molybdenum, and silicon; alloys including aluminum, tin, zirconium, niobium, molybdenum, and silicon; alloys including aluminum, molybdenum, tin, and silicon; alloys including aluminum, tin, zirconium, and molybdenum; alloys including aluminum, vanadium, chromium, zirconium, and molybdenum; alloys including molybdenum, niobium, aluminum, and silicon; alloys including vanadium, chromium, tin, and aluminum; or alloys including palladium, but are not limited thereto. For example, they may be Ti-6Al-4V, Ti-6Al-7Nb, Ti-13Nb-13Zr, Ti-8Al-1Mo-1V, Ti-6Al-6V-2Sn, Ti-35.3Nb-5.1Ta-7.1Zr, Ti-29Nb-13Ta-4.6Zr, Ti-29Nb-13Ta-2Sn, Ti-29Nb-13Ta-4.6Sn, Ti-29Nb-13Ta-6Sn, Ti-16Nb-13Ta-4Mo, Ti-6Al-5Zr-0.5Mo-0.2Si, Ti-6Al-2Sn-4Zr-2Mo-0.08Si, Ti-5.5Al-3.5Sn-3Zr-1Nb-0.5Mo-0.3Si, Ti-6Al-3Sn-4Zr-0.5Mo-0.5-Si, Ti-4Al-4Mo-2Sn-0.5Si, Ti-4Al-4Mo-4Sn-0.5Si, Ti-6Al-2Sn-4Zr-6Mo, Ti-3Al-8V-6Cr-4Zr-4Mo, Ti-15Mo-3Nb-3Al-0.2Si, Ti-15V-3Cr-3Sn-3Al, or Ti/Pd, all of which are commercially available, but are not limited thereto, and any titanium alloys, which can be used for implants, can be used without limitation.

Preferably, the oxidative etching can be performed for 1 hour to 12 hours, more preferably for 1 hour to 6 hours, but is not limited thereto. In addition, preferably, the oxidative etching can be performed at 0° C. to 30° C., more preferably at 4° C. to 20° C., but is not limited thereto. Herein, the mixed etching composition may be used in an amount such that the implant for surface treatment can be sufficiently immersed. Also, the etching can be performed by applying the mixed etching composition only to a desired part, or selectively performed by partially immersing the implant in the mixed etching composition.

Preferably, in order to improve the safety when inserted into the body, a washing process may be further performed to remove excess etching composition after the oxidative etching. The washing of the surface-treated implant may be performed by a conventional method known in the art, and is not specifically limited thereto. For example, it may be performed by ultrasonication by immersing the implant in solvents such as distilled water, acetone, methanol, ethanol, etc. using an ultrasonic washing machine.

Preferably, the method for preparing an implant of the present invention may further comprise treating by a machining method, atmospheric pressure plasma treatment, vacuum plasma treatment, high temperature plasma treatment, metal beads sintering method, particle blasting method, acid treatment, alkali treatment, anodic oxidation method, ion implantation method, or a combination thereof, but is not limited thereto. Micrometer-sized bumps are formed by a well-known method in the art and are then treated with the mixed etching composition of the present invention comprising hydrogen peroxide and a carbonate compound to further form porous bump structures in the level of small micrometers and nanometers, and thus, the implant may have various hierarchical surface structures.

In the second aspect, the present invention provides a titanium or titanium alloy implant which is prepared by oxidative etching with the mixed etching composition comprising hydrogen peroxide and a water-soluble carbonate compound.

The implant according to the present invention is characterized in that it has micrometer-sized irregular bumps and channel-shaped nanometer-sized bumps on the surface thereof. As described above, the complex bump structures in micrometer and nanometer levels formed on the surface of the implant significantly increase the surface area and surface energy, increasing hydrophilicity and at the same time, increasing the surface adsorption of cell adhesion-mediated proteins including fibronectin and various growth factors present in the body fluid, thereby promoting adhesion, proliferation, and differentiation of osteogenic cells, and osseointegration of the implant.

Preferably, the implant may be prepared according to the method for preparing an implant of the present invention.

Specifically, the morphological characteristics of the surface of the titanium metal alloys treated according to the examples of the present invention were evaluated, and as a result, when the titanium metal alloys were immersed in the mixed etching composition comprising hydrogen peroxide and a carbonate compound, it was observed that micrometer-sized and nanometer-sized bump structures were simultaneously formed. The formation of such bump structures occurs when the carbonate compound is added to hydrogen peroxide, the pH of the hydrogen peroxide aqueous solution increases, and at the same time, the metal ions generated from the inserted titanium alloys and the carbonate react together with hydrogen peroxide to produce hydroxyl radicals, perhydroxyl radicals, and superoxide anion radicals, all of which have a strong oxidizing power, and thus, the surface of the titanium metal alloys undergoes a strong oxidative etching to form the bump structures. In addition, such oxygen radicals are applied to the surface of the titanium metal alloys immersed in the etching composition to form nano-channel bumps, thereby forming micrometer-sized bump structures through continuous oxidative etching.

The implant of the present invention is not limited to a form, and any form can be applied to the implant. Preferably, the implant may be in the form of a screw, block, plate, film, filament, membrane, mesh, woven fabric, non-woven fabric, knit, granule, particle, bolt, nut, nail, or a combination thereof, but is not limited thereto, and as long as the implant can be inserted into the body, it is not limited to the form thereof.

The implant of the present invention is characterized in that the implant made of titanium or a titanium alloy is treated with an environmentally friendly etching composition to have micrometer-sized bumps on the surface thereof and at the same time have channel-shaped nanometer-sized bumps irregularly formed on the bump structures above. Accordingly, it is harmless when inserted into the body, and the contact and/or binding areas with the surrounding tissue cells remarkably increase, thereby showing significantly increased a new bone formation promoting effect and an osseointegration effect due to improved bone tissue reaction. Therefore, the implant may be inserted into the body and used to replace damaged tissue or promote regeneration of the tissue. In addition, it may be used for the purpose of supporting or treating damaged or lost skeletal tissues. For example, it may be used as supports, joints, devices for bone fixation, spinal fixation, etc. for regenerating and supporting various hard tissues including dental and orthopedic implants, abutments, artificial bones, artificial joints, jaw bone and small bones in the facial region, fillers, ceramics, brackets, core, post, etc. Preferably, the implant of the present invention may be used as artificial tooth roots, artificial implant fixture, artificial joints, or artificial bones, but is not limited thereto.

In another aspect, the present invention provides a composition for treating a surface of an implant comprising hydrogen peroxide and a water-soluble carbonate compound.

Preferably, the composition for treating a surface of an implant may include hydrogen peroxide in an amount of 1 wt % to 98 wt % relative to the total weight of the composition. More preferably, the composition may include hydrogen peroxide in an amount of 10 wt % to 50 wt %, but is not limited thereto.

Preferably, the composition for treating a surface of an implant may include a carbonate compound in an amount of 0.01 wt % to 90 wt % relative to the total weight of the composition. More preferably, the composition may include the carbonate compound in an amount of 0.5 wt % to 20 wt %, but is not limited thereto.

Meanwhile, the method for preparing an implant according to the fourth aspect of the present invention is a method for preparing an implant on which surface bumps having continuous or discontinuous line-shaped open channel nanoscale structures are irregularly formed, wherein the method comprises preparing an etching composition comprising hydrogen peroxide and a basic solution; and oxidatively etching an implant made of titanium or a titanium alloy by immersing the same in the etching composition.

Without limitation, the sponge-like microscale network structures and bumps having continuous or discontinuous line-shaped channel nanoscale structures may be irregularly formed together on the titanium or titanium alloy implant by the etching composition.

The hydrogen peroxide may be included in an amount of 1 wt % to 98 wt % relative to the total weight of the composition. Preferably, the hydrogen peroxide may be included in an amount of 5 wt % to 50 wt %, and more preferably in an amount of 10 wt % to 50 wt %, but is not limited thereto.

The non-limiting examples of the available basic solutions include aqueous solutions containing NaOH, KOH, $Ca(OH)_2$, $NH_4OH$, $NH_3$, $Mg(OH)_2$, $Fe(OH)_3$, $Al(OH)_3$, $CH_3NH_2$, and/or $NaHCO_3$, etc. The basic solution is not limited to a type and the amount of used as long as hydroxyl radicals, perhydroxyl radicals, and superoxide anion radicals having a strong oxidizing power are generated upon a reaction with hydrogen peroxide, and thereby inducing a strong oxidative etching on the surface of the titanium metal alloys.

The basic solution is not limited to the amount of used as long as the etching composition maintains the pH range of 2 to 8, preferably, the pH range of 6 to 7.

The description of the terms, preferable embodiments, and the principles thereof with respect to the fourth aspect are the same as those explained in the method for preparing an implant according to the first aspect and the implant according to the second aspect.

The titanium or titanium alloy implant according to the fifth aspect of the present invention is prepared by oxidative etching with the etching composition containing hydrogen peroxide and a basic solution, and is characterized in that surface bumps having continuous or discontinuous line-shaped open channel nanoscale structures are irregularly formed.

FIG. 10 illustrates images of the nanostructure of the surface of the implant which underwent oxidative etching with the etching composition containing hydrogen peroxide and NaOH, and it can be confirmed that sponge-like microscale network structures and bumps having continuous or discontinuous line-shaped channel nanoscale structures are irregularly formed.

The description of the titanium or titanium alloy implant according to the fifth aspect of the present invention is the same as that described in the implant according to the second aspect.

BEST MODE

Hereinafter, the present invention will be described in more detail. However, the following examples are provided for illustrative purposes only, and the scope of the present invention should not be limited thereto in any manner.

Example 1

Surface Treatment of Titanium Alloys by Etching Composition Including Hydrogen Peroxide/Sodium Bicarbonate Titanium alloys were subject to a surface treatment using a mixed etching composition including hydrogen peroxide ($H_2O_2$) and sodium bicarbonate ($NaHCO_3$). Ti-6Al-4V having a 10 mm diameter, which is a commercial titanium alloy, was cut into 3 mm thick and made into cylindrical discs. The surface of the titanium alloy discs was polished by SiC abrasive sandpapers up to #1200 stepwise and then ultrasonically cleaned in acetone, alcohol, and distilled water in sequence for 15 minutes each to prepare titanium alloy samples. Meanwhile, 5 g of sodium bicarbonate was added to 100 ml of 30 wt % hydrogen peroxide aqueous solution, and was completely dissolved to prepare a mixed etching composition including hydrogen peroxide/sodium bicarbonate. The pH of the composition was maintained at 7.4. Hereinafter, the mixed etching composition including hydrogen peroxide/sodium bicarbonate is referred to as HPC. A beaker containing HPC was transferred to a wide container filled with tap water, and two titanium alloys were soaked into the beaker containing HPC. The titanium alloy discs were allowed to stand at room temperature for 4 hours and subject to oxidative etching, and then were ultrasonically washed in acetone, alcohol, and distilled water in sequence for 20 minutes each. The washed samples were dried in a sterile workbench in air and stored in a desiccator.

The morphological characteristics of the surface of the titanium alloys treated with HPC were observed by scanning electron microscope (SEM), and the results were illustrated in FIG. 1. As shown in FIG. 1, microscale or nanoscale bumps were simultaneously formed on the surface treated with HPC. Also, the roughness (Ra) of the surface treated with HPC was measured with a profilometer and showed a value of 0.72±0.08.

Example 2

Surface Treatment of Titanium Alloys by Etching Composition Including Hydrogen Peroxide/Ammonium Bicarbonate Titanium alloys were subject to a surface treatment using a mixed etching composition including hydrogen peroxide and ammonium bicarbonate ($NH_4HCO_2$). The titanium alloy samples were prepared in the same manner as described in Example 1. In addition, 3 g of ammonium bicarbonate was added to 100 ml of 30 wt % hydrogen peroxide aqueous solution and completely dissolved to prepare a mixed etching composition including hydrogen peroxide/ammonium bicarbonate. A beaker containing the mixed etching composition including hydrogen peroxide/ammonium bicarbonate was transferred to a wide container filled with tap water, and two prepared titanium alloys were soaked into the beaker containing the mixed etching composition including hydrogen peroxide/ammonium bicarbonate. The titanium alloy discs were allowed to stand at room temperature for 5 hours and subject to oxidative etching, and then were ultrasonically washed in acetone, alcohol, and distilled water in sequence for 20 minutes each. The washed samples were dried in a sterile workbench in air and stored in a desiccator.

The morphological characteristics of the surface of the titanium alloys treated with the mixed etching composition including hydrogen peroxide/ammonium bicarbonate were observed by SEM, and the results were illustrated in FIG. 2. As shown in FIG. 2, it was confirmed that the surface treated with the mixed etching composition including hydrogen peroxide/ammonium bicarbonate shows surface characteristics similar to the surface treated with HPC according to Example 1. That is, the microscale or nanoscale bumps were simultaneously formed on the surface treated with the mixed etching composition including hydrogen peroxide/ammonium bicarbonate. Also, the roughness (Ra) of the surface treated with the mixed etching composition including hydrogen peroxide/ammonium bicarbonate was measured with a profilometer and showed a value of 0.62±0.08.

Example 3

Surface Treatment of Titanium Alloys by Etching Composition Including Hydrogen Peroxide/Magnesium Bicarbonate Titanium alloys were subject to a surface treatment using a mixed etching composition including hydrogen peroxide and magnesium bicarbonate ($Mg(HCO_3)_2$). The titanium alloy samples were prepared in the same manner as described in Example 1. In addition, 3 g of magnesium bicarbonate was added to 100 ml of 30 wt % hydrogen peroxide aqueous solution and completely dissolved to prepare a mixed etching composition including hydrogen peroxide/magnesium bicarbonate. A beaker containing the mixed etching composition including hydrogen peroxide/magnesium bicarbonate was transferred to a wide container filled with tap water, and two prepared titanium alloy discs were soaked into the beaker containing the mixed etching composition including hydrogen peroxide/magnesium bicarbonate. The titanium alloy discs were allowed to stand at room temperature for 2 hours and subject to oxidative etching, and then were ultrasonically washed in acetone, alcohol, and distilled water in sequence for 20 minutes each. The washed samples were dried in a sterile workbench in air and stored in a desiccator.

The morphological characteristics of the surface of the titanium alloys treated with the mixed etching composition including hydrogen peroxide/magnesium bicarbonate were observed by SEM, and the results were illustrated in FIG. 3. As shown in FIG. 3, it was confirmed that the surface treated with the mixed etching composition including hydrogen peroxide/magnesium bicarbonate shows surface characteristics similar to the surface treated with HPC according to Example 1.

Example 4

Surface Treatment of Titanium Alloys by Etching Composition Including Hydrogen Peroxide/Calcium Carbonate Titanium alloys were subject to a surface treatment using a mixed etching composition including hydrogen peroxide and calcium carbonate ($CaCO_3$). The titanium alloy samples were prepared in the same manner as described in Example 1. In addition, 3 g of calcium carbonate was added to 100 ml of 30 wt % hydrogen peroxide aqueous solution and completely dissolved to prepare a mixed etching composition including hydrogen peroxide/calcium carbonate. A beaker containing the mixed etching composition including hydrogen peroxide/calcium carbonate was transferred to a wide container filled with tap water, and two prepared titanium alloys were soaked into the beaker containing the mixed etching composition including hydrogen peroxide/calcium carbonate. The titanium alloy discs were allowed to stand at room temperature for 6 hours and subject to oxidative etching, and then were ultrasonically washed in acetone, alcohol, and distilled water in sequence for 20 minutes each. The washed samples were dried in a sterile workbench in air and stored in a desiccator.

The morphological characteristics of the surface of the titanium alloys treated with the mixed etching composition including hydrogen peroxide/calcium carbonate were observed by SEM, and the results were illustrated in FIG. 4. As shown in FIG. 4, it was confirmed that the surface treated with the mixed etching composition including hydrogen peroxide/calcium carbonate shows surface characteristics similar to the surface treated with HPC according to Example 1.

Example 5

Surface Treatment of Titanium Alloys by Etching Composition Including

Hydrogen Peroxide/Sodium Carbonate

Titanium alloys were subject to a surface treatment using a mixed etching composition including hydrogen peroxide and sodium carbonate ($Na_2CO_3$). The titanium alloy samples were prepared in the same manner as described in Example 1. In addition, 3 g of sodium carbonate was added to 100 ml of 30 wt % hydrogen peroxide aqueous solution and completely dissolved to prepare a mixed etching composition including hydrogen peroxide/sodium carbonate. A beaker containing the mixed etching composition including hydrogen peroxide/sodium carbonate was transferred to a wide container filled with tap water, and two prepared titanium alloys were soaked into the beaker containing the mixed etching composition including hydrogen peroxide/sodium carbonate. The titanium alloy discs were allowed to stand at room temperature for 12 hours and subject to oxidative etching, and then were ultrasonically washed in acetone, alcohol, and distilled water in sequence for 20 minutes each. The washed samples were dried in a sterile workbench in air and stored in a desiccator.

The morphological characteristics of the surface of the titanium alloys treated with the mixed etching composition including hydrogen peroxide/sodium carbonate were observed by SEM, and the results were illustrated in FIG. 5. As shown in FIG. 5, it was confirmed that the surface treated with the mixed etching composition including hydrogen peroxide/sodium carbonate shows surface characteristics similar to the surface treated with HPC according to Example 1.

Example 6

Surface Treatment of Titanium Alloys by Etching Composition Including Hydrogen Peroxide/Calcium Bicarbonate Titanium alloys were subject to a surface treatment using a mixed etching composition including hydrogen peroxide and calcium bicarbonate ($Ca(HCO_3)_2$). The titanium alloy samples were prepared in the same manner as described in Example 1, except that Ti-6Al-7Nb was used instead of Ti-6Al-4V. In addition, 3 g of calcium bicarbonate was added to 100 ml of 30 wt % hydrogen peroxide aqueous solution and completely dissolved to prepare a mixed etching composition including hydrogen peroxide/calcium bicarbonate. A beaker containing the mixed etching composition including hydrogen peroxide/calcium bicarbonate was transferred to a wide container filled with tap water, and two prepared titanium alloys were soaked into the beaker containing the mixed etching composition including hydrogen peroxide/calcium bicarbonate. The titanium alloy discs were allowed to stand at room temperature for 4 hours and subject to oxidative etching, and then were ultrasonically washed in acetone, alcohol, and distilled water in sequence for 20 minutes each. The washed samples were dried in a sterile workbench in air and stored in a desiccator.

The morphological characteristics of the surface of the titanium alloys treated with the mixed etching composition including hydrogen peroxide/calcium bicarbonate were observed by SEM, and as a result, it was confirmed that the surface treated with the mixed etching composition including hydrogen peroxide/calcium bicarbonate shows surface characteristics similar to the surface treated with HPC according to Example 1.

Example 7

Surface Treatment of Titanium Alloys by Etching Composition Including Hydrogen Peroxide/Potassium Bicarbonate Titanium alloys were subject to a surface treatment using a mixed etching composition including hydrogen peroxide and potassium bicarbonate ($KHCO_3$). The titanium alloy samples were prepared in the same manner as described in Example 1, except that Ti-13Nb-13Zr was used instead of Ti-6Al-4V. In addition, 1 g of potassium bicarbonate was added to 100 ml of 30 wt % hydrogen peroxide aqueous solution and completely dissolved to prepare a mixed etching composition including hydrogen peroxide/potassium bicarbonate. A beaker containing the mixed etching composition including hydrogen peroxide/potassium bicarbonate was transferred to a wide container filled with tap water, and two prepared titanium alloys were soaked into the beaker containing the mixed etching composition including hydrogen peroxide/potassium bicarbonate. The titanium alloy discs were allowed to stand at room temperature for 8 hours and subject to oxidative etching, and then were ultrasonically washed in acetone, alcohol, and distilled water in sequence for 20 minutes each. The washed samples were dried in a sterile workbench in air and stored in a desiccator.

The morphological characteristics of the surface of the titanium alloys treated with the mixed etching composition including hydrogen peroxide/potassium bicarbonate were observed by SEM, and as a result, it was confirmed that the surface treated with the mixed etching composition including hydrogen peroxide/potassium bicarbonate shows surface characteristics similar to the surface treated with HPC according to Example 1.

Example 8

Surface Treatment of Titanium Alloys by Etching Composition Including Hydrogen Peroxide/Potassium Carbonate Titanium alloys were subject to a surface treatment using a mixed etching composition including hydrogen peroxide and potassium carbonate ($K_2CO_3$). The titanium alloy samples were prepared in the same manner as described in Example 1, except that Ti-8Al-1Mo-1V was used instead of Ti-6Al-4V. In addition, 10 g of potassium carbonate was added to 100 ml of 30 wt % hydrogen peroxide aqueous solution and completely dissolved to prepare a mixed etching composition including hydrogen peroxide/potassium carbonate. A beaker containing the mixed etching composition including hydrogen peroxide/potassium carbonate was transferred to a wide container filled with tap water, and two prepared titanium alloys were soaked into the beaker containing the mixed etching composition including hydrogen peroxide/potassium carbonate. The titanium alloy discs were allowed to stand at room temperature for 1 hour and subject to oxidative etching, and then were ultrasonically washed in acetone, alcohol, and distilled water in sequence for 20 minutes each. The washed samples were dried in a sterile workbench in air and stored in a desiccator.

The morphological characteristics of the surface of the titanium alloys treated with the mixed etching composition including hydrogen peroxide/potassium carbonate were observed by SEM, and as a result, it was confirmed that the surface treated with the mixed etching composition including hydrogen peroxide/potassium carbonate shows surface characteristics similar to the surface treated with HPC according to Example 1.

Example 9

Surface Treatment of Titanium Alloys by Etching Composition Including Hydrogen Peroxide/Silver Carbonate Titanium alloys were subject to a surface treatment using a mixed etching composition including hydrogen peroxide and silver carbonate ($Ag_2CO_3$). The titanium alloy samples were prepared in the same manner as described in Example 1, except that Ti-6Al-6V-2Sn was used instead of Ti-6Al-4V. In addition, 2 g of silver carbonate was added to 100 ml of 30 wt % hydrogen peroxide aqueous solution and completely dissolved to prepare a mixed etching composition including hydrogen peroxide/silver carbonate. A beaker containing the mixed etching composition including hydrogen peroxide/silver carbonate was transferred to a wide container filled with tap water, and two prepared titanium alloys were soaked into the beaker containing the mixed etching composition including hydrogen peroxide/silver carbonate. The titanium alloy discs were allowed to stand at room temperature for 6 hours and subject to oxidative etching, and then were ultrasonically washed in acetone, alcohol, and distilled water in sequence for 20 minutes each. The washed samples were dried in a sterile workbench in air and stored in a desiccator.

The morphological characteristics of the surface of the titanium alloys treated with the mixed etching composition including hydrogen peroxide/silver carbonate were observed by SEM, and as a result, it was confirmed that the surface treated with the mixed etching composition including hydrogen peroxide/silver carbonate shows surface characteristics similar to the surface treated with HPC according to Example 1.

Comparative Example 1

Surface Treatment of Titanium Alloys by SLA Method

The titanium alloys were subject to a surface treatment by the SLA method, which is a conventional surface treatment method for implants. The Ti-6Al-4V titanium alloy samples were prepared in the same manner as described in Example 1. The Grit blasting was performed on the titanium alloy samples using hydroxyapatite particles with a size of 100 μm, and the remaining particles used in the grit blasting were removed using a nitric acid solution and then ultrasonically washed in acetone, alcohol, and distilled water in sequence for 15 minutes each. The washed titanium alloys were dried in a sterile workbench in air, and subsequently, they were soaked in a mixed solution containing 67% hydrochloric acid and sulfuric acid at a volume ratio of 1:1 and subject to acid etching at 80° C. for 20 minutes. The titanium alloys treated with the acid were ultrasonically washed in acetone, alcohol, and distilled water in sequence for 15 minutes each, dried in a sterile workbench in air, and stored in a desiccator.

Experimental Example 1

Microstructure of Surface Treated-Titanium Alloys by

Mixed Etching Composition Including Hydrogen Peroxide/Carbonate

The surface morphological microstructures of the titanium alloys whose surface was treated with the mixed etching composition including hydrogen peroxide and various carbonate compounds according to Examples 1 to 5 were observed by SEM, and the results were illustrated in FIGS. 1 to 5.

As shown in FIGS. 1 to 5, it was confirmed that bumps (pores) having a size of several to several tens of micrometers were irregularly formed on the surface of the titanium alloys treated with the mixed etching composition including hydrogen peroxide and carbonate compounds, as irregular sponge-like network structures (FIGS. 1A to 5A). It was confirmed in the high-magnification SEM images thereof that the bumps in the size of several to several tens of nanometers were formed in a regularly oriented comb-shape such that the nano-channels with pores opened towards the surface were formed (FIGS. 1B to 5B).

As such, although the type of the carbonate compounds and/or the treatment time used in each example were different, the micrometer-sized bumps and the nanometer-sized bumps having open channel structures on the bump structures above were formed on the surface of the titanium alloys treated with the mixed etching composition including hydrogen peroxide/carbonate compounds.

Experimental Example 2

Roughness of Surface of Surface Treated-Titanium Alloy Discs

The roughness of the surface of the titanium alloys treated according to Examples 3 to 5 and Comparative Example 1 using a profilometer. As described above, the micrometer-sized bumps, and the nanometer-sized bumps having open channel structures on the micrometer-sized bump structures above were formed on the surface of the titanium alloys treated with the mixed etching composition including hydrogen peroxide/carbonate compounds, regardless of the types of carbonate used. Further, in order to confirm the effect according to the treatment time of the composition, the roughness of the titanium surface treated for different times (2 hrs, 6 hrs, and 12 hrs), which were prepared according to Examples 3 to 5, was measured and the results were illustrated in FIG. 6. The titanium alloy discs treated with SLA were used as the control group.

As the treatment time increased, the micrometer-sized bumps were formed in a larger and wider size whereas the shape of the nanometer-sized bumps formed on the bumps above started to become irregular (FIGS. 3 to 5).

Experimental Example 3

Wettability of Surface of Surface-Treated Titanium Alloy Discs

The wettability of the surface of the titanium alloy discs treated according to Example 1 and Comparative Example 1 was analyzed by an instrument for surface contact angle using water drops, and the results were illustrated in FIG. 7. The contact angle measured at the surface of Comparative Example 1 was 76°, and it was impossible to measure the contact angle at the surface of Example 1 as water droplet was immediately dispersed as soon as it made contact with the surface. Further, the same observation was seen with the surface of the titanium alloy discs treated according to Examples 2 to 9 as with the surface of Example 1. This implies that the surfaces treated with the mixed etching composition including hydrogen peroxide and carbonate compound according to the present invention show remarkably excellent wettability.

Experimental Example 4

Evaluation of Cell Culture and Bone Formation on Surface of Surface-Treated Titanium Alloy Discs The cell proliferation and bone formation were evaluated on the surface of the titanium alloy discs treated according to Example 1 and Comparative Example 1. Specifically, MC3T3-E1 cells derived from mouse calvaria, which are osteoblast-like cells, were aliquoted in each prepared disc at a density of $1 \times 10^4$ cell/disc and cultured. The cell proliferation was evaluated by MTT assay (3-(4,5-dimethylthiazol-2-yl)-2,5-diphenyltetrasodium bromide), and the bone formation was evaluated by measuring the activity of alkaline phosphatase (ALP).

The cells were aliquoted on the surface of the titanium alloys of Example 1 (HPC treatment) and Comparative Example 1 (SLA treatment) and subsequently collected at day 3, day 5, and day 7 to confirm the cell proliferation, and the results were illustrated in FIG. 8. As shown in FIG. 8, there was no significant difference in terms of cell proliferation until day 3 of culture, but it was confirmed that the rate of cell proliferation on days 5 and day 7 of culture significantly increased on the HPC-treated surface compared to the SLA-treated surface (n=7, $P<0.001$, One-way ANOVA Statistic analysis results).

Further, the ALP activity was measured on days 7 and 14 of culture to confirm the bone formation according to the culturing time on the titanium alloy surface of Example 1 and Comparative Example 1, and the results thereof were illustrated in FIG. 9. As shown in FIG. 9, when the cells were cultured for 9 days on the titanium alloy surface treated with HPC, the cells showed a significantly higher ALP activity compared to those cultured on the titanium alloy surface treated with SLA for the same period of time. Also, the difference was even more significant on day 14 of culture (n=7, $P<0.001$, One-way ANOVA statistic analysis results).

As such, the surface of the titanium alloy treated with the mixed etching composition including hydrogen peroxide and carbonate compounds according to the present invention includes the micrometer-sized bumps and channel-shaped nanometer-sized bumps and thus has an increased surface area, can have improved wettability, and can effectively promote cell proliferation and osteocyte differentiation, and therefore, the mixed etching composition can be useful for implant surface treatment.

Example 10

Surface Treatment of Titanium Alloys by Etching Composition Including Hydrogen Peroxide/Sodium Hydroxide Titanium alloys were subject to a surface treatment using a mixed etching composition including hydrogen peroxide ($H_2O_2$) and sodium hydroxide (NaOH). The titanium alloy samples were prepared in the same manner as described in Example 1. In addition, 0.5 g of sodium hydroxide was added to 100 ml of 30 wt % hydrogen peroxide aqueous solution and completely dissolved to prepare a mixed etching composition having a pH of 7.4. A beaker containing the mixed etching composition including hydrogen peroxide/sodium hydroxide was transferred to a wide container filled with tap water, and two titanium alloys were soaked into the beaker containing the mixed etching composition including hydrogen peroxide/sodium hydroxide. The titanium alloy discs were allowed to stand at room temperature for 4 hours and subject to oxidative etching, and then were ultrasonically washed in acetone, alcohol, and distilled water in sequence for 20 minutes each. The washed samples were dried in a sterile workbench in air and stored in a desiccator.

The morphological characteristics of the surface of the titanium alloys treated with the mixed etching composition including hydrogen peroxide/sodium hydroxide were observed by SEM, and the results were illustrated in FIG. 10. As shown in FIG. 10, it was confirmed that the surface treated with the mixed etching composition including hydrogen peroxide/sodium hydroxide showed surface characteristics similar to the surface treated with HPC according to Example 1, and when the roughness (Ra) of the surface was measured with a profilometer, the results showed a value of 0.81±0.08. Further, it was confirmed that the surface wettability was increased as shown in FIG. 11, and that the cell proliferation and differentiation were superior compared to the SLA treatment as shown in FIGS. 12 and 13.

The invention claimed is:

1. A method of preparing a titanium or titanium alloy implant, the surface of which has various hierarchical surface structures comprising (a) micrometer-sized sponge-like network structures of at least 1 micrometer and (b) continuous or discontinuous line-shaped open channel-shaped nanometer-sized bumps less than 100 nanometers formed on the micrometer-sized structures above, in such a way that a surface hydrophilicity and wettability of the surface of the titanium or titanium alloy implant has been increased by further imposing the hierarchical surface structures on the titanium or titanium alloy implant, said method comprising:
preparing a mixed etching composition with a pH of 7 to 8, comprising hydrogen peroxide, a base, and water; and
oxidatively etching an implant that does not comprise the micrometer-sized structures, the implant being made of titanium or a titanium alloy, by immersing the same in the mixed etching composition in such way that the hierarchical surface structures of the titanium or titanium alloy implant are formed by the oxidatively etching,
wherein the hierarchical surface structures of the titanium or titanium alloy implant lead to increasing the contact and/or binding areas with cells and increasing the titanium or titanium alloy implant's surface adsorption of protein or growth factor present in a body fluid, as well as promoting adhesion, proliferation or differentiation of cells as compared to an implant without said hierarchical surface structures, and
wherein the method does not comprise the use of a strong acid.

2. The method of claim 1, wherein the hydrogen peroxide is selected from the group consisting of an aqueous solution of hydrogen peroxide, solid hydrogen peroxide, urea hydrogen peroxide ($CO(NH_2)_2 \cdot H_2O_2$), sodium percarbonate ($2Na_2CO_3 \cdot 3H_2O_2$), and a mixture thereof.

3. The method of claim 1, wherein the base is a water-soluble carbonate compound selected from the group consisting of a bicarbonate compound, a carbonate compound, and a mixture thereof.

4. The method of claim 1, wherein the titanium alloy further comprises at least one material selected from the group consisting of aluminum, tantalum, niobium, vanadium, zirconium, tin, molybdenum, silicon, gold, palladium, copper, platinum, and silver.

5. The method of claim 1, wherein the oxidative etching is performed at 0° C. to 30° C.

6. The method of claim 1, wherein the method further comprises treating by a machining method, atmospheric pressure plasma treatment, vacuum plasma treatment, plasma treatment, metal beads sintering method, particle blasting method, acid treatment, alkali treatment, anodic oxidation method, ion implantation method, or a combination thereof.

7. The method of claim 1, wherein the base is a water-soluble carbonate compound.

8. The method of claim 1, wherein the base is selected from the group consisting of NaOH, KOH, $Ca(OH)_2$, $NH_4OH$, $NH_3$, $Mg(OH)_2$, $Fe(OH)_3$, $Al(OH)_3$, $CH_3NH_2$, and $NaHCO_3$.

9. The method of claim 1, wherein the etching step is performed for 1 to 12 hours.

* * * * *